United States Patent [19]
Weissman

[11] 3,932,939
[45] Jan. 20, 1976

[54] PIN ARRANGEMENT FOR PROSTHODONTIC CASTS

[76] Inventor: Bernard Weissman, 225 E. 48th St., New York, N.Y. 10017

[22] Filed: Aug. 8, 1973

[21] Appl. No.: 386,722

[52] U.S. Cl............................................. 32/2; 32/11
[51] Int. Cl.²......................................... A61C 13/00
[58] Field of Search ............. 32/2, 11, 40 R, 71, 13, 32/10 A; 16/2

[56] References Cited
UNITED STATES PATENTS

| | | | |
|---|---|---|---|
| 2,655,724 | 10/1953 | Brooks | 32/13 |
| 2,705,837 | 4/1955 | Gerlach | 32/13 |
| 3,704,519 | 12/1972 | Lystager | 32/11 |

FOREIGN PATENTS OR APPLICATIONS

| | | | |
|---|---|---|---|
| 894,771 | 3/1943 | France | 32/13 |

Primary Examiner—Russell R. Kinsey
Assistant Examiner—J. Q. Lever
Attorney, Agent, or Firm—Freidman & Goodman, Esqs.

[57] ABSTRACT

A dental model cast includes an impression of at least one tooth and a substantially flat surface opposingly disposed relative to the tooth impression. The dental model cast is in the form of a plurality of segments. Each of the segments is removably mounted on a base cast and can be replaced in their original positions thereon. Extending from the flat surface of each segment is an elongate brass pin which is provided with a tapered free end. Each segment is also provided with a shorter tapered or conical pin which is made from an elastomeric material such as polyethylene. The base casting is provided with a polyethylene sleeve configurated to receive a portion of the tapered brass pin which extends beyond the flat surface. A tapered or conical opening is provided in the base cast which is configurated to receive the shorter tapered pin. The brass pin acts as a locating pin which initially engages and locates the opening in the sleeve while the shorter tapered pin acts as an alignment pin which is received in the tapered opening in the base cast to align and fix the position of the dental model cast relative to the base cast. The pins forming part of the prosthodontic cast model as well as the method of forming the latter is also described.

21 Claims, 18 Drawing Figures

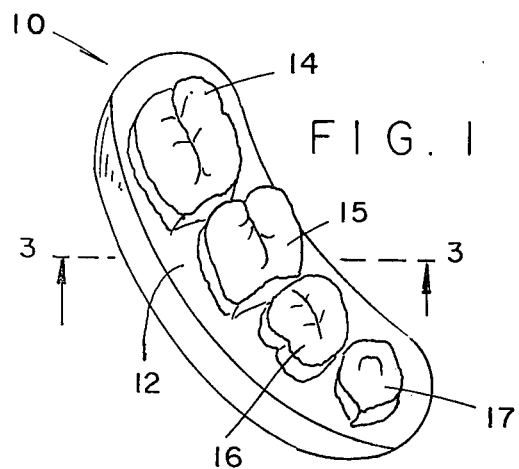
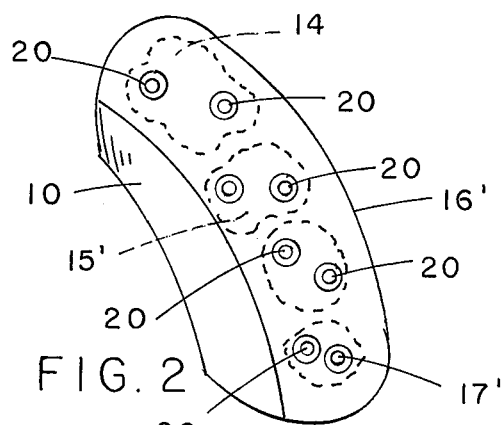
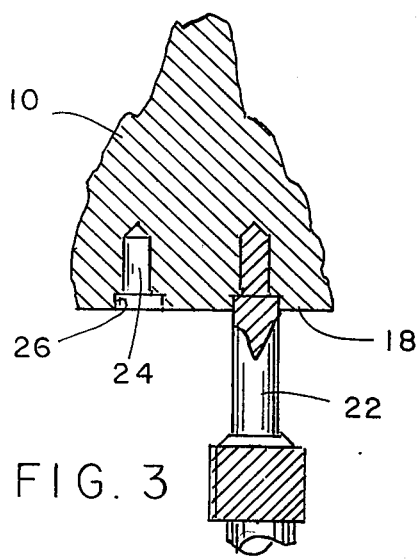
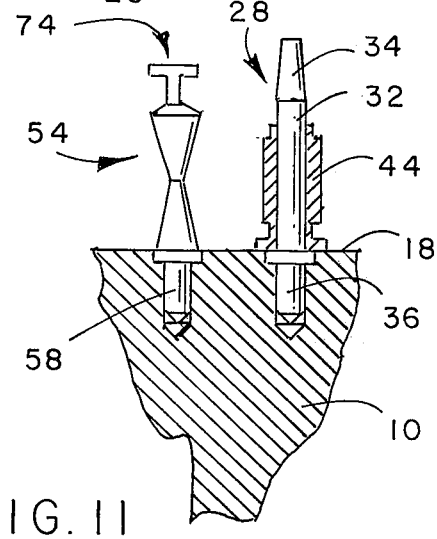
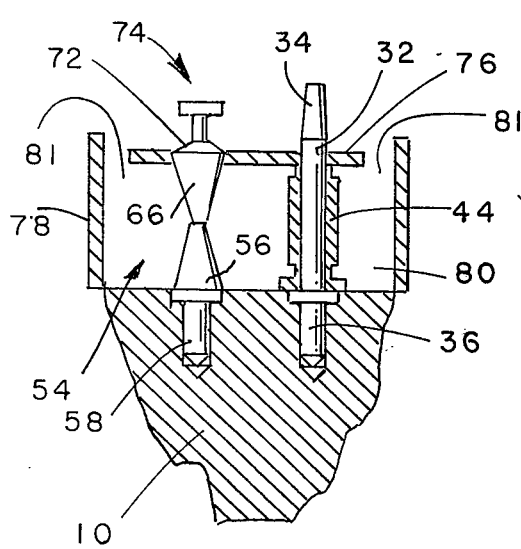
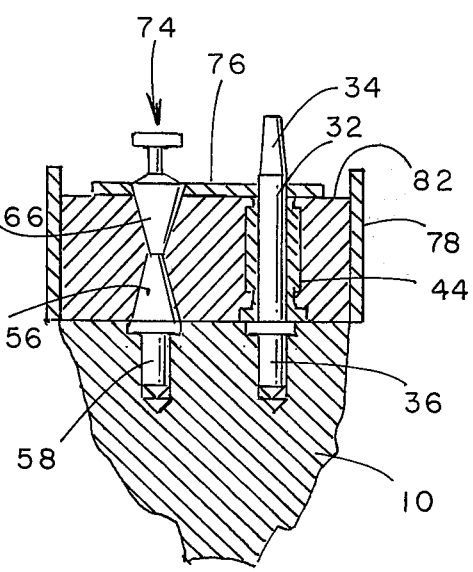

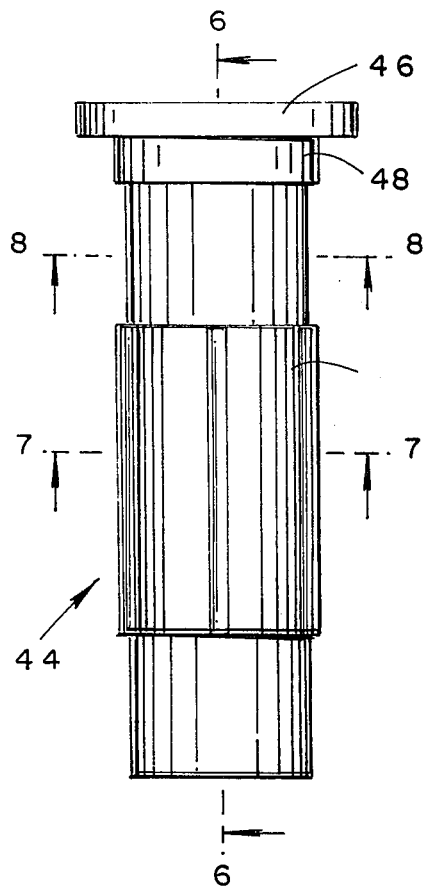
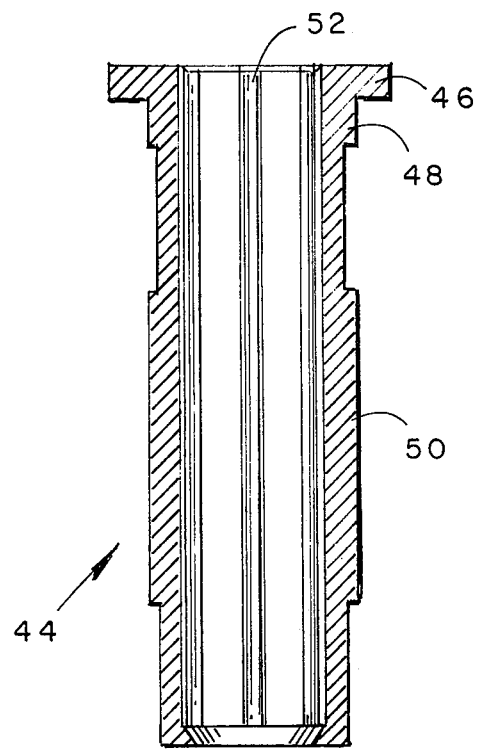
FIG. 5  FIG. 6
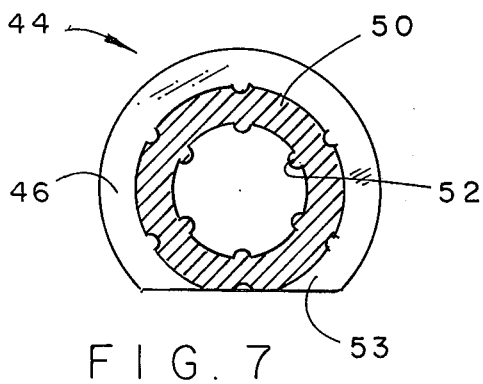
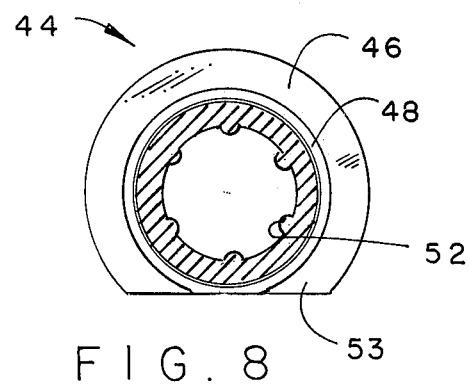
FIG. 7  FIG. 8

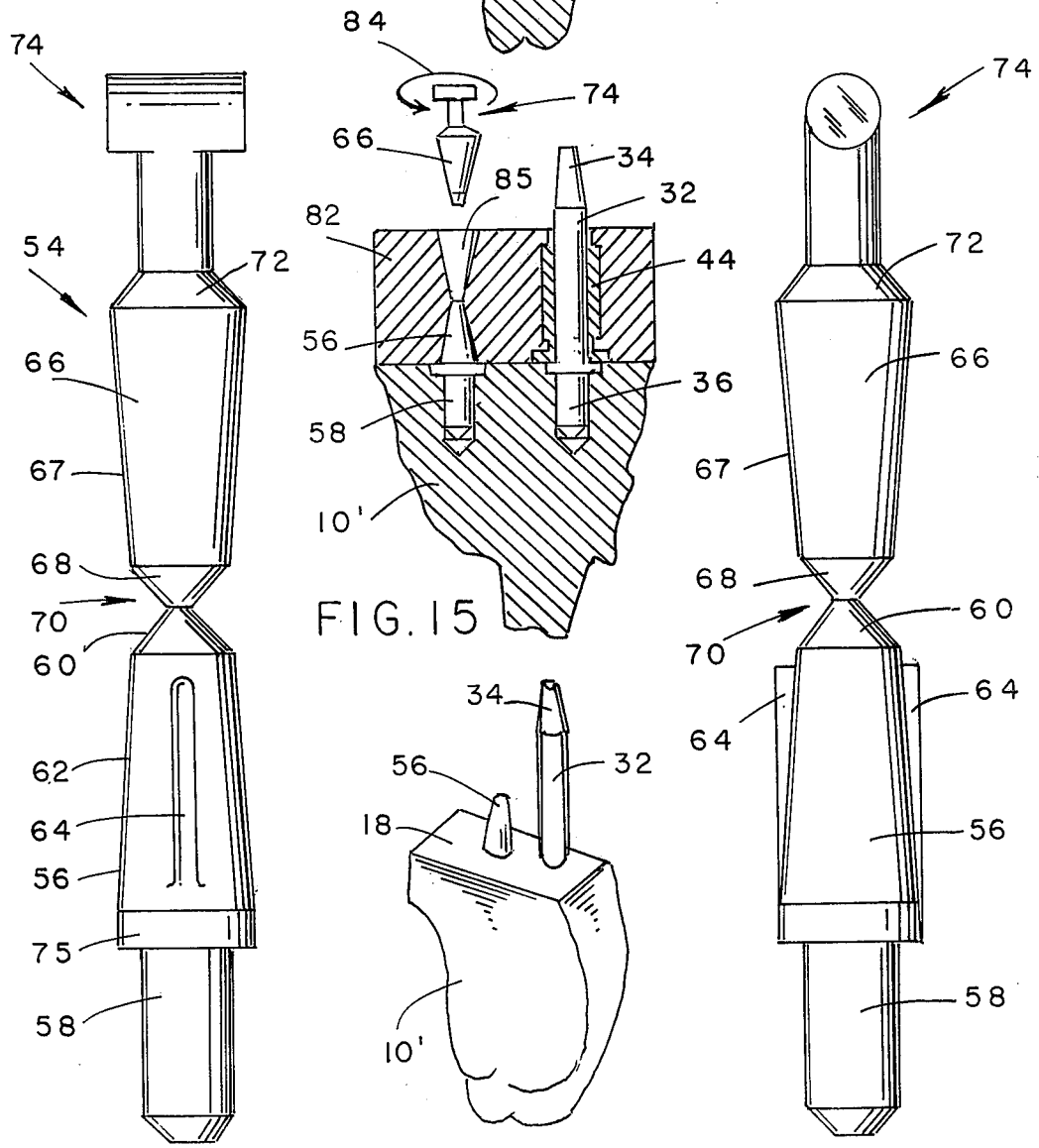

PIN ARRANGEMENT FOR PROSTHODONTIC CASTS

BACKGROUND OF THE INVENTION

The present invention generally relates to prosthodontic casts, and more particularly to an improvement in the pins and sleeves which permit the separation and simple replacement in original positions of the segments on a base cast.

Prosthodontics denote that branch of the dental art or science that specifically treats the replacement of missing dental and oral tissues. The basic art of dental prosthodontics is well known. Many specialized procedures have been worked out for making crowns, inlays, bridge work and the like. In this type of work, it is customary to make an impression in rubber or a similar material by making an impression in a tray. The tray is generally filled with a suitable impression material, such as wax, hydrocolloid and the like. The dental impression tray, with the impression material therein, is placed in the patient's mouth and results in a negative impresssion of the tooth or teeth upon which the work is to be performed. The hardened dye is generally provided on the underside with dowel pins that are used in a base so that the die may be separated from the base and removed therefrom to facilitate working thereon. The setting of the dowel pins both relative to the die and to each other is extremely important if the segments, which are to be removed for closer scrutiny, are to be replaced in proper alignment. It frequently happens that the work is to be performed on only one or a group of teeth at a time. By making it possible to remove small segments from the overall die or cast, the work is facilitated to a great extent.

Various pins and bushings are already known in the prior art. However, most of the known pins have disadvantages which have limited their usefulness. Thus, for example, according to one known pin design, all the pins are of the same length and extend equal distances above the surface in which they are embedded. Such an arrangement is disclosed in U.S. Pat. No. 3,704,519. This pin design has the disadvantage that when it is desired to replace a segment on the cast, it is difficult to align the two or more pins simultaneously before the pins may be inserted into the corresponding bushings.

According to another pin design, the free extending ends of the pins are cylindrical and of uniform diameter. This design has the disadvantage that the pins must be perfectly centered with respect to the openings of the bushings before insertion can be achieved. In both cases, replacement of segments is inconvenient and time consuming.

A still further disadvantage of many of the prior art prosthodontic casts arrangements is that the base cast onto which the segments are mounted is frequently substantially thicker than the length of the pins which they receive. Consequently, the pins do not fully extend through the base cast and the pins are accessible therethrough when the segments are mounted on the base cast. This has the disadvantage that the pins cannot be externally reached for applying pressure thereon and removing a segment when the pins become stuck within the openings in the base cast. Consequently, application of forces directly to the dental model casts may damage or break the same when the pins are frozen within their associated apertures or holes.

SUMMARY OF THE INVENTION

Accordingly, it is an object of the present invention to provide a pin arrangement for prosthodontic casts which is not possessed of the above disadvantages.

It is another object of the present invention to provide a pin arrangement as described above which is simple in construction and economical to manufacture.

It is still another object of the present invention to provide a pin arrangement of the type under discussion which insures proper alignment of segments which have been separated from a base cast.

It is a further object of the present invention to provide a pin arrangement for prosthodontic casts which is simple and convenient to align when replacing a removed segment onto a base cast.

It is yet a further object of the present invention to provide a pin arrangement which minimizes the play existent between the pins and the bushings in which they are inserted to thereby insure correct alignment and ease of segment replacement onto a base cast.

It is yet a further object of the present invention to provide a pin arrangement for prosthodontic casts which facilitate the mounting of the pins in the casts.

It is an additional object of the present invention to provide a pin arrangement for prosthodontic casts which provides passageways in the base casts opposite the pin receiving apertures to thereby make the pins accessible exteriorly of the base cast when the segments are mounted on the base casts.

It is still an additonal object of the present invention to provide pins which can be utilized in connection with prosthodontic casts and which facilitate assembly as well as the utilization of these casts.

It is yet an additional object of the present invention to provide a method of mounting pins on a dental cast to form a dental model having removable and replaceable segments as suggested in the above objects.

In order to achieve the above objects, as well as others which will become apparent hereafter, the present invention, for a dental model of teeth wherein segments thereof may be individually removed and replaced in original positions, comprises a first cast forming an impression of at least one tooth on one surface thereof and having a substantially flat surface in opposed relation to said one surface. A second cast is provided with a substantially flat surface for abutting against said flat surface of said first cast. At least two pins are provided which are embedded in said first cast each having different length projections extend beyond said flat surface of said first cast. Said second cast is provided with openings in the flat surfaces thereof configurated to receive at least portions of said pins when said flat surfaces are in abutment against one another. In this manner, the pin with the longer projection is a locating pin which initially engages and locates a corresponding opening in said second cast and the pin with the shorter projection is an alignment pin which is received in a corresponding opening to align and fix the position of said first cast relative to said second cast.

Advantageously, said pin provided with the longer projection is substantially cylindrical and is made from a noncorrosive metal such as brass. Said shorter projection is advantageously conical with the apex thereof pointed away from said flat surface of said first cast and is made from an elastomeric material such as polyethylene.

In the presently preferred embodiment, a sleeve is provided in said second cast which is configured to receive said longer extension, the sleeve advantageously being made from an elastomeric material such as polyethylene.

A pin for use with the dental model comprises a shank and an annular collar extending about said shank to divide the latter into first and second shank portions. In this manner, one of said shank portions in said collar is suitable for being embedded in a dental model cast while the other shank portion extends beyond the dental model cast to be received in a corresponding aperture of a base cast on which the dental model cast is to be mounted. Advantageously, the free end of said one shank is tapered to facilitate location or insertion of the free end into an associated opening or sleeve in said base cast.

A sleeve for receiving the shank of a pin embedded in a dental model comprises a tubular member having an axis. An annular shoulder is disposed at and surrounds one end of said sleeve. In this manner, a shank of a pin may initially slidably abut against said annular shoulder, when the latter is exposed, prior to being guided into said sleeve. Advantageously, the sleeve is provided with longitudinal ribs parallel to said axis both along the exterior as well as the interior surfaces thereof.

A second type of pin or alignment member for aligning a dental model cast of the base cast comprises a pair of pins connected at a weakened line portion and tapered towards one another. In this manner, one of said pins has a portion thereof adapted to be fixed in the dental cast and is receivable in a tapered aperture in the case coat. The other of said pins is adapted to be embedded in and extend beyond the base cast to permit gripping the other of said pins and twisting the latter to separate the same from said one pin and provide a passageway in the base cast through which said one pin can be externally reached.

A method in accordance with the present invention comprises the steps of forming at least two openings in a flat surface of the dental model cast. An end of a pin is inserted into each of said openings. The other ends of the pins are embedded into a base cast having a thickness less than the lengths of said other ends of the pins to cause the latter to at least partially extend beyond the base cast when the latter abuts against said flat surface.

In the presently preferred method, a sleeve is mounted on the other end of at least one of said pins prior to said embedding step.

When one of said pins comprises two tapered portions connected to each other at a narrow weakened portion, the method further comprises the step of severing said tapered portions at said weakened portion by gripping one of the tapered portions extending beyond said base casts, when said casts are in abutment against each other, and twisting the gripped tapered portion relative to the other tapered portion embedded in said dental model cast.

BRIEF DESCRIPTION OF THE DRAWINGS

With the above and additional objects and advantages in view, as will hereinafter appear, this invention comprises the devices, combinations and arrangements of parts hereinafter described and illustrated in the accompanying drawings of a preferred embodiment in which:

FIG. 1 is a perspective view of a dental model cast, showing the impressions of teeth formed along one surface thereof;

FIG. 2 is a rear perspective view of the dental model cast of FIG. 1, showing a substantially flat surface disposed opposite from the surface on which the tooth impressions are formed, and further showing the outlines of the teeth formed on the other side and markings at which holes are to be drilled for receiving alignment pins;

FIG. 3 is a fragmented cross section of the surface shown in FIG. 2, showing a drill forming holes in the dental model cast at the locations designated by the markings shown in FIG. 2;

FIG. 5 is a front elevational view of a sleeve in accordance with the present invention;

FIG. 6 is a cross section of the sleeve shown in FIG. 5, taken along line 6—6;

FIG. 7 is a cross section of the sleeve shown in FIG. 5, taken along line 7—7;

FIG. 8 is a cross section of the sleeve shown in FIG. 5, taken along line 8—8;

FIG. 9 is a front elevational view of a second pin in accordance with the present invention utilized in the formation of the prosthodontic casts;

FIG. 10 is a front elevational view of the pin shown in FIG. 9;

FIG. 11 is a fragmented cross sectional view of the dental model cast shown in FIG. 3, inverted and having portions of the pins shown in FIGS. 4, 9 and 10 received in the drilled holes in the cast, and showing a sleeve such as shown in FIG. 5 mounted on the shank or extension of the pin shown in FIG. 4;

FIG. 12 is similar to FIG. 11, further showing a substantially enclosed space formed by placing wax sheets or paper about the pins;

FIG. 13 is similar to FIG. 12 and showing a plaster base cast poured within the space defined by the wax sheets to embed the pins;

FIG. 14 is similar to FIG. 13 with the wax sheets or paper removed after the plaster base casts has hardened;

FIG. 15 is similar to FIG. 14, showing the manner in which a removable pin is severed from an alignment pin by twisting a gripping portion which extends beyond the base cast;

FIG. 18 is a perspective view of one of the segments formed from the dental cast model which includes the two pins in accordance with the present invention.

DETAILED DESCRIPTION OF THE PREFERRED EMBODIMENTS

Figure 17:
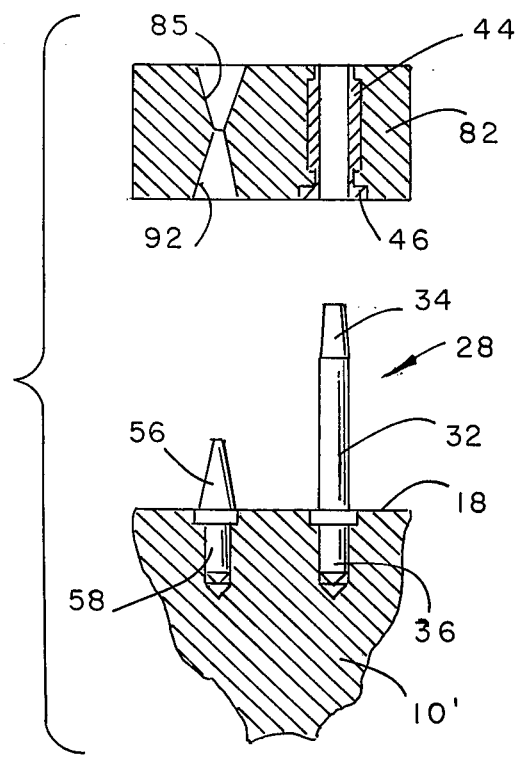
FIG. 17 is similar to FIG. 14, showing one of the segments which have been broken off from the dental model cast separated from the base cast, the positioning and orientation of the segments relative to the base cast being specifically defined by the two pins.

Referring now to the FIGURES, in which the same reference numerals are utilized to designate similar or identical parts throughout, and first referring to FIG. 1, positive cast or a dental model is generally designated by the reference numeral 10 and is of the type which is formed from an impression tray in accordance with techniques well known in the art. The dental cast model 10 has a surface 12 on which are formed tooth impressions 14–17. In FIG. 2, the underside of the dental cast model 10 is provided with a substantially flat surface 18. The dashed tooth outlines 14'–17' respectively represent the tooth impressions formed on the opposed surface 12.

As will become apparent hereafter, the dental model cast 10 can be cut into segments to include one or more tooth impressions. The segments can be cut in any desired fashion. However, the present invention utilizes two pins for fixing the location of each segment relative to a base cast to be described. Accordingly, markings 20 are provided on each anticipated segment for indicating where holes are to be drilled. The specific locations of the marks 20 are not critical, and any convenient locations which does not damage the mold or crowd the holes may be utilized.

In FIG. 3, a drill bit 22 is shown to drill holes 24 which are provided with countersinks 26. The holes 24 are drilled in the flat underside or bottom surface 18 at the points where the marks 20 have been provided. The drilling operation can be performed on a drilling machine for plaster casts or models as described in U.S. application Ser. No. 320,275, filed Jan. 2, 1973.

After all the holes 24 have been drilled in the surface 18 at the locations indicated by the marks 20, the dental model 10 is inverted to bring the bottom surface 18 into an upwardly facing horizontal position as shown in FIG. 11.

Figure 4:
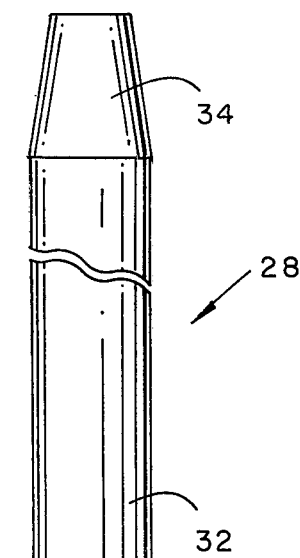
FIG. 4 is a fragmented front elevational view of a locating pin in accordance with the present invention.

A pin 28, best shown FIG. 4, is partially inserted into one of the holes 24 associated with each tooth or tooth outline, shown in FIG. 2. The pin 28 is provided with an annular collar or flange 30 which divides the shank of the pin into a long end or shank 32 which forms an extension or projection above the surface 18, as to become clear hereafter. The shank 32 is provided with a taper 34 to facilitate location as to be described.

On the other side of the annular collar or flange 30 is a short end or shank 36 whose length is selected to be approximately equal to the length of the holes 24. The free end of the shank 36 is provided with a chamber 38 which facilitates insertion of the shank 36 into the hole 24. The diameter of the annular collar 30 is selected to be approximately equal to the diameter of the countersink 26, whereby the latter receives the annular collar 30 with little clearance therebetween. In the presently preferred embodiment, adhesive is provided between the collar 30, shank 36 and the hole 24 which fixes the position of the pin 28 on the dental model 10. The difference in length between the long and short shanks 32 and 36 is not critical and the shanks may be equal or different in length, with different degrees of advantage. In the presently preferred embodiment, the pin 28, which is to be designated as a locating pin, is made from a noncorrosive material and may be made of any noncorrosive metal such as brass. Advantageously, the external surface of the long shank or extension 32 is provided with a smooth finish to facilitate insertion of the shank 32 into an aperture or opening to be described hereafter.

Referring to FIGS. 5–8 and FIG. 11, a tubular sleeve or bushing 44 is placed over the long extension or shank 32. The sleeve 44 is provided with an annular shoulder 46 at one free end thereof which is substantially planar and extends in a radial direction. Inside the annular shoulder 46 is provided an annular collar 48 which is utilized to anchor the sleeve 44 within a cast, as to be described hereafter. For reasons which will become more apparent from the description that follows, the sleeve 44 is provided with elongate external ribs 40 which extend in a longitudinal direction. In the presently preferred embodiment, the external ribs 50 extend only along a partial axial length of the sleeve. However, it should be clear, that the external ribs 50 can extend along the entire length of the sleeve.

Extending along the interior surface of the sleeve 44 are spaced internal ribs 52 which extend longitudinally of the sleeve. The internal ribs 52 extend radially inwardly, together defining a cavity dimensioned to receive the shank 32 with small clearance therebetween. Advantageously, the sleeve 44 is made from a somewhat resilient material such as polyethylene. Any other suitable elastomeric material may be utilized for this purpose. In this manner, the shank 32 is slidably receivable within the sleeve 44 with slight frictional engagement therebetween. In this manner, the sleeve 44, while it can be placed onto and removed from the extension or shank 32 with facility does not undesirably freely move relative thereto.

When placing the sleeve 44 on the shank or extension 32, the end bearing the annular shoulder 46 is first placed over the pin so that the annular shoulder comes into abutment with the surface 18 when the sleeve 44 is lowered to the position shown in FIG. 10. In this position, the annular shoulder 46 abuts against the flat surface 18.

Referring to FIGS. 7 and 8, it will be noted that the annular shoulder 46 is provided with a cutaway portion 53. In the presently preferred embodiment, the cutaway portion 53 permits the positioning of two sleeves 44 adjacently to one another, where space limitations so require. Although the cutaway portion 53 is illustrative of the manner in which the sleeve 44 can be modified to accommodate space limitations, other ways of cutting the sleeve 44 are also possible.

Referring to FIGS. 9-11, an alignment member 54 is shown which is disposed within the second hole 24 associated with a second point mark 20 within each tooth outline. Consequently, the two tooth marks 20 within each tooth outline shown in FIG. 2 define the positions of two holes 24 one of which receives a pin 28 while the other of the holes of each set receives an alignment member 54.

As best shown in FIGS. 9 and 10, the alignment member 54 comprises an alignment pin 56 provided with a chamfered shank 58 extending at the free end thereof, and a taper 60 at the other end thereof. Advantageously, the alignment pin 56 is provided with a taper 62 which increases in diameter from the region of the shank 58 to the taper 60. Further, the alignment pin 56 is provided with fins 64 which project radially as shown in the FIGS. 9 and 10. Although two fins 64 are shown in the presently preferred embodiment, any suitable number desired may be utilized.

Connected to the alignment pin 56 is a removable pin 66 provided with a taper 67 which tapers in an opposite sense as the taper 62. At the narrowed end of the taper 67 there is provided a steeper taper 68. The tapers 60 and 68 are connected to one another at a weakened portion 70 which structurally forms the weakest portion of the alignment member 54.

At the enlarged end of the taper 67 there is provided an inverse taper forming a neck 72 from which extends a gripping portion 74 whose purpose will be described hereafter.

The pins 56 and 66 are configured to be separated at the weakened portion 70 as to be described.

Provided between the tapers 62 and the shank 58 is a cylindrical portion 75 which is dimensioned to be received within the countersink 26 of a hole 24.

As with the pin 28, the shank 58 of the alignment member 54 is inserted into one of the holes 24, lowering the cylindrical portion 75 within the countersink of the hole. In the presently preferred embodiment, any suitable adhesive is provided on the inner surface of the hole and on the shank 58 to retain the alignment member 54 in fixed relation on the dental model 10.

Advantageously, the alignment member 54 is integrally constructed and is made from a somewhat resilient material such as polyethylene.

An important feature of the present invention is that the length of the alignment pin 56, extending from the cylindrical portion 75 to the narrowest portion of the taper 60, is shorter than the length of the shank or extension 32. The reason for this different length will be described hereafter.

After the shanks 36 and 58 of a respective locating pin 28 and an alignment member 54 have been inserted into a pair of holes 24 within a respective tooth outline, with a bushing or sleeve 44 disposed over the pin 28 as shown in FIG. 11, a wax sheet 76, substantially parallel to the now horizontal flat surface 18, is disposed over the pin and alignment member as shown in FIG. 12. The wax sheet 76 is provided with apertures or holes which are adapted to receive the upper ends or portions of the pins and alignment members. By selecting the holes provided in the wax sheets 76 sufficiently small, the wax sheets 76 can rest in the position shown on the upper free end of the sleeve 44 and on the neck 72 of the alignment members.

A further wax sheet 78 is disposed about the periphery of the surface 18 to form a dam or a substantially vertical wall which, together with the wax sheet 76, defines a substantially closed space 80. However, the wax sheet 76 is selected to be somewhat smaller than the surface 18 to thereby provide at least one space 81 which provides access to the interior of the space 80.

To be noted in FIG. 12 is that both the alignment pin 56 as well as the removable pin 66 is enclosed within the space 80. In this manner, when a plaster or any other suitable material utilized for this purpose is poured into the space 80, as shown in FIG. 13, both the alignment pin as well as the removable pin is embedded within the plaster 82. The precise extent to which the removable pin 66 is embedded within the plaster base 82 is not critical for the purpose of the present invention. However, the gripping portion 74 should, in any event, extend beyond the plaster base 82 to permit gripping the same, for example, with human fingers. With respect to the pin 28 and the sleeve 44, the plaster base 82 is poured to fully embed the sleeve 44 but advantageously not to extend beyond. In this manner, the plaster 82 does not physically come into contact with the pin 28 and the pin 28 continues, when the model is fully assembled, to only slidably move or extend through the sleeve 44.

After the plaster 82 has hardened, the wax sheets or paper 76 and 78 can be removed as shown in FIG. 14. To prevent adhesion between the plaster or base cast 82 and the dental model 10, any suitable lubricant or other material utilized for this purpose may be provided on the surface 18 prior to the pouring of the plaster 82. In this manner, the base cast 82 can be removed or separated from the dental model 10 with great facility, as shown in FIG. 17.

Referring to FIGS. 14 and 15, the gripping portion 74 is gripped at this time, such as with one's fingers, and is twisted in one or the other direction about the axis generally defined by the alignment member 54, as suggested by the arrow 84. For the reason that the removable pin 66 is somewhat resilient, as well as because adhesion betweeen a smooth elastomeric surface and plaster is minimal, the removable pin 66 can be twisted and severed from the alignment pin 56 at the region portion 70. The fins 64, embedded in the base cast 82, prevent corresponding rotation of the alignment pin 56. The taper 67 of the removable pin 66 permits removal of the pin 66 from the base cast 82, as shown in FIG. 15. The opening or aperture 85 formed thereby exposes the now free end of the alignment pin 56. An important feature of the present invention is that while the alignment pin 56 is substantially shorter than the shank 32 and is shorter than the thickness of the base cast 82, the pin 56 is nevertheless accessible from the exterior of the base cast. The resulting passageway or aperture 85 in the base cast 82 permits the alignment pin to be externally reached for the purpose of applying pressures thereto when the dental model 10 is frozen or becomes inseparable from the base cast 82. At such time, a long thin object can be disposed within the passageway 85 and the aligment pin 56 can be gently tapped in the direction of the dental model 10. In this manner, the dental model 10 can be conveniently separated from the base cast 82. For the same reason, it will be noted that the shank 32 extends beyond the base cast 82. The purpose for this is to provide access to the pin 28 externally of the plaster cast 82 when the latter fully contains or receives the locating pin as shown in FIG. 15. With such construction, the dental model 10 can always be removed or separated from the base cast 82 without the need to apply direct tensil forces on the dental model 10 which may damage the latter.

Figure 16:
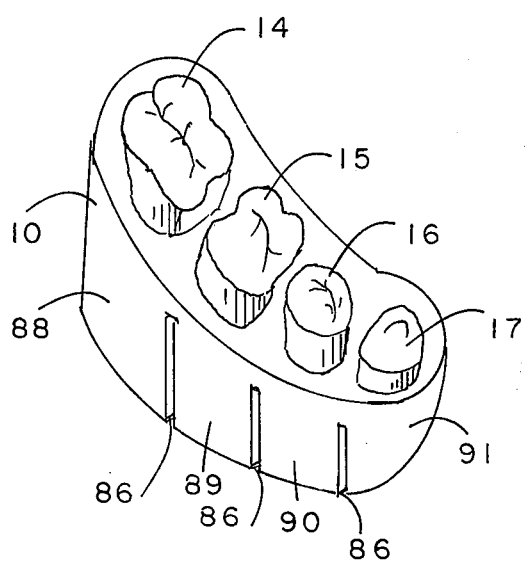
FIG. 16 is similar to FIG. 1, further showing a series of cuts formed in the dental model cast between the teeth to form a plurality of segments.

After the locating pins 28 and alignment members 54 have been respectively inserted into each pair of holes associated with each tooth outline, cuts 86 may be made in the dental model, as shown in FIG. 16. The cuts are made in any conventional manner to permit formation of individual segments 88–91 each including a respective tooth 14–17. The cuts 86 may be made in any desired fashion. However, as suggested above, each resulting segments is to include one locating pin 28 and one alignment pin 56. A typical segment 10' is shown in FIGS. 17 and 18. In FIG. 17 and 10' is shown separated from the base cast 82. The aperture or tapered hole 92 is formed in the casting process by the alignment pin 56.

Removal of the segment 10' may be achieved, as suggested above, by gently applying pressure on the shank 32 which extends beyond the base cast 82. Such pressure is generally sufficient to separate the base cast from the segment. If necessary, a gentle pressure may be applied to the alignment pin 56 through the passageway or aperture 85 by any suitable implement.

The present construction of the dental model provides an extremely simple method of replacing the segments in their original aligned positions prior to removal or separation from the base cast. The procedure involves aligning the segment in essentially opposed relation to the associated portion of the base cast 82 as suggested in FIG. 17. The dental model segment 10' is advanced towards the base cast 82, the tapered end 34 first coming into contact with the base cast. Typically, prior to insertion of the shank 32 within the sleeve 44, due to possible error judgments in position, the tapered end 34 of the pin 28 initially contacts and slidably abuts against the annular shoulder 46 of the sleeve 44. In this manner, the annular shoulder 46 prevents damage to the plaster surrounding the sleeve 44 after repeated removals and replacements of the segments.

Location of the opening in the sleeve by the tapered end 34 of the pin 28 is achieved by minipulating the segment 10' and moving the latter in abutting relation against the annular shoulder 46. Once the shank 32 has been received within the sleeve 44, the segment 10' has been located with respect to the base cast 82. Now, the segment 10' can be further moved towards the base cast 82 while the shank 32 is increasingly received within the sleeve 44. Advancement of the segment 10' towards the base cast 82 continues in this manner to the extent permitted by the alignment 56. If the alignment pin 56 is directly or immediately received within the tapered hole 92, the segment 10' may be fully advanced to thereby bring the surface 18 into abutment with the base cast 82. On the other hand, if the segment 10' is angularly misaligned with respect to the base cast 82, the segment 10' must be turned about the axis of the shank 32 to bring the alignment 56 into alignment with the tapered hole 92. When this occurs, full advancement of the segment 10' towards the base cast 82 may be achieved. Clearly, alignment of the pins 28 and 56 into the sleeve 44 and taperered hole 92 respectively completely fixes the position and angular orientation of the segment 10' relative to the base cast 82. Once total advancement of the segment 10' is achieved relative to the base cast 82, as described above, the position of the segment 10' is fully defined and fixed in its original position.

The present construction, as described above, overcomes the disadvantages of the prior art. Firstly, the locating pin 28 and the alignment pin 56 are tapered and only one of these pins must be received in an associated opening. This greatly facilitates location and alignment of the segments relative to the base cast. Additionally, the segments can be easily removed or separated from the base cast. When the pins become stuck in the base cast 82, for any reason, means are provided for separating the segments from the base cast without any danger to the dental model segment.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. In a dental model of teeth, wherein segments thereof may be individually removed and replaced in original positions, a first cast forming an impression of at least one tooth on one surface thereof and having a substantially flat surface in opposed relation to said one surface; and second cast provided with a substantially flat surface for abutting against said flat surface of said first cast; at least two pins embedded in said first cast each having different length projections extending beyond said flat surface of said first cast, said second cast being provided with openings in the flat surface thereof configurated to receive at least portions of said pins when said flat surfaces are in abutment against one another, whereby the pin with the longer projection is a locating pin which initially engages and locates a corresponding opening in said second cast and the pin with the shorter projection is an alignment pin which is received in a corresponding opening to align and fix the position of said first cast relative to said second cast.

2. In a dental model as defined in claim 1, wherein said pin provided with the longer projection is substantially cylindrical and has a tapered free end.

3. In a dental model as defined in claim 1, wherein said pin provided with the longer projection is made from a non-corrosive metal.

4. In a dental model as defined in claim 1, wherein said shorter projection is conical with the apex thereof pointed away from said flat surface of said first cast.

5. In a dental model as defined in claim 1, wherein said pin provided with the shorter projection is made from an elastomeric material.

6. In a dental model as defined in claim 5, wherein said material is polyethylene.

7. In a dental model as defined in claim 1, further comprising a sleeve embedded in said second cast configurated to receive said longer extension.

8. In a dental model as defined in claim 7, wherein the axial length of said sleeves corresponds to the thickness of said second cast and is shorter than said longer extension, whereby said longer extension is received in and extends beyond said sleeve and said second cast when said flat surfaces are in abutment against one another.

9. In a dental model as defined in claim 7, wherein said sleeve is provided with longitudinal ribs on the exterior surface thereof.

10. In a dental model as defined in claim 7, wherein said sleeve is provided with longitudinal ribs on the interior surface thereof.

11. In a dental model as defined in claim 7, wherein said sleeve is provided with an annular shoulder disposed and surrounding one end of said sleeve, whereby said longer extension may initially contact and slidably abut against said annular shoulder prior to be guided into said sleeve.

12. A sleeve for receiving the shank of a pin embedded in a dental model, said sleeve comprising a tubular member having an axis, an annular shoulder disposed at and surrounding one end of said sleeve, whereby a shank of a pin may initially slidably abut against said annular shoulder when the latter is exposed prior to being guided into said sleeve, and longitudinal ribs extending at least along one of the interior and exterior surfaces of said sleeve.

13. A sleeve as defined in claim 12, wherein said tubular member is made from an elastomeric material.

14. A sleeve as defined on claim 13, wherein said material is polyethylene.

15. A method of mounting pins on a dental model cast for removing and replacing the same in original positions on a base cast, and wherein one of said pins comprises two tapered portions connected to each other at a narrow weakened portion, the method comprising the steps of forming at least two openings in a flat surface of the dental model cast; inserting an end of a pin into a respective one of said openings; and embedding the other ends of the pins into a base cast having a thickness less than the lengths of said other ends of the pins to cause the latter to at least partially extend beyond the base cast when the latter abuts against said flat surface; and severing said tapered portions at said weakened portion by gripping one of the latter extending beyond said base cast when said casts are in abutment against each other and tearing the gripped tapered portion relative to the other tapered portion embedded in said dental model cast.

16. A method as defined in claim 15, wherein said tearing step comprises twisting the gripped tapered portion about its axis relative to the tapered portion fixed in the dental model cast.

17. An alignment member for aligning a dental model cast with a base cast, said alignment member comprising a pair of pins connected at a weakened line portion and tapered towards one another, whereby one of said pins has a portion thereof adapted to be fixed in the dental model cast and is receiveable in a tapered aperature in the base cast, the other of said pins being adapted to be embedded in and extend beyond the base cast to permit gripping the other of said pins and twisting the latter to separate the same from said one pin and provide a passageway in the base cast through which said one pin can be extremely reached, and longitudinal fin means being provided on said one of said pins for preventing rotation of the latter when embedded in the base cast.

18. An alignment member as defined in claim 17, wherein said other of said pins includes a gripping portion which can be gripped to twist one pin relative to the other to separate said pins at said weakened portion.

19. An alignment member as defined in claim 17, wherein said pins are made from an elastomeric material.

20. An alignment member as defined in claim 19, wherein said material is polyethylene.

21. An alignment member as defined in claim 17, wherein said one of said pins is provided with a shank receivable in a corresponding aperture in the dental model cast.

* * * * *